US008007579B2

(12) United States Patent  
Klettke et al.

(10) Patent No.: US 8,007,579 B2  
(45) Date of Patent: Aug. 30, 2011

(54) POLYETHER-BASED PREPARATIONS AND USE THEREOF

(75) Inventors: Thomas Klettke, Diessen (DE); Bernd Kuppermann, Herrsching (DE); Hendrik M. Grupp, Woerthsee (DE)

(73) Assignee: 3M Innovative Properties Company, St. Paul, MN (US)

( * ) Notice: Subject to any disclaimer, the term of this patent is extended or adjusted under 35 U.S.C. 154(b) by 232 days.

(21) Appl. No.: 12/375,245

(22) PCT Filed: Jul. 24, 2007

(86) PCT No.: PCT/US2007/074162
§ 371 (c)(1),
(2), (4) Date: Jan. 27, 2009

(87) PCT Pub. No.: WO2008/014224
PCT Pub. Date: Jan. 31, 2008

(65) Prior Publication Data
US 2009/0311651 A1 Dec. 17, 2009

(30) Foreign Application Priority Data
Jul. 28, 2006 (EP) ..................................... 06015830

(51) Int. Cl.
*A61C 9/00* (2006.01)
(52) U.S. Cl. ........ 106/38.2; 528/405; 528/417; 433/214
(58) Field of Classification Search .................. 523/109, 523/15–108; 528/26, 29; 556/15–109
See application file for complete search history.

(56) References Cited

U.S. PATENT DOCUMENTS

| | | | | | |
|---|---|---|---|---|---|
| 1,010,000 | A | * | 11/1911 | Snyder | 92/107 |
| 1,294,946 | A | * | 2/1919 | Pupilla | 118/16 |
| 1,374,144 | A | * | 4/1921 | Farrell | 89/41.02 |
| 1,745,810 | A | * | 2/1930 | Pickett | 362/282 |
| 1,846,029 | A | * | 2/1932 | Froussard | 12/31.5 |
| 2,374,144 | A | * | 4/1945 | Stikeleather | 29/890.048 |
| 2,765,323 | A | * | 10/1956 | Dixon et al. | 552/296 |
| 2,978,276 | A | * | 4/1961 | Huffman | 403/1 |
| 3,453,242 | A | * | 7/1969 | Zahler et al. | 528/322 |
| 3,505,377 | A | | 4/1970 | Morehouse | |
| 3,980,688 | A | | 9/1976 | Litteral et al. | |
| 4,093,555 | A | * | 6/1978 | Schmitt et al. | 525/132 |
| 4,160,776 | A | | 7/1979 | Scardera et al. | |
| 4,167,618 | A | * | 9/1979 | Schmitt et al. | 528/424 |
| 4,176,618 | A | * | 12/1979 | Hubert | 116/102 |
| 4,226,794 | A | | 10/1980 | Scardera et al. | |
| 4,337,168 | A | | 6/1982 | Scardera et al. | |
| 4,431,789 | A | | 2/1984 | Okazaki et al. | |
| 4,493,911 | A | * | 1/1985 | Schmitt et al. | 523/109 |
| 4,505,225 | A | * | 3/1985 | Husain | 118/669 |
| 4,532,268 | A | * | 7/1985 | Jochum et al. | 523/109 |
| 4,657,959 | A | | 4/1987 | Bryan et al. | |
| 4,761,136 | A | | 8/1988 | Madhavan et al. | |
| 4,778,832 | A | * | 10/1988 | Futami et al. | 523/109 |
| 4,813,875 | A | | 3/1989 | Hare | |
| 4,877,845 | A | * | 10/1989 | Parks et al. | 525/346 |
| 4,877,854 | A | * | 10/1989 | Hattori et al. | 528/15 |
| 5,052,195 | A | * | 10/1991 | Lunt | 63/21 |
| 5,052,197 | A | * | 10/1991 | Fleissner | 68/5 D |
| 5,086,148 | A | * | 2/1992 | Jochum et al. | 528/15 |
| 5,100,929 | A | | 3/1992 | Jochum et al. | |
| 5,130,348 | A | * | 7/1992 | Zahler et al. | 523/109 |
| 5,177,120 | A | | 1/1993 | Hare et al. | |
| 5,323,436 | A | * | 6/1994 | Lee | 377/17 |
| 5,569,691 | A | | 10/1996 | Guggenberger et al. | |
| 5,750,589 | A | | 5/1998 | Zech et al. | |
| 5,830,951 | A | * | 11/1998 | Fiedler | 525/478 |
| 5,849,812 | A | * | 12/1998 | Zech et al. | 523/109 |
| 5,850,921 | A | | 12/1998 | Shindou et al. | |
| 5,955,513 | A | | 9/1999 | Hare | |
| 6,029,782 | A | * | 2/2000 | Chojecki et al. | 188/170 |
| 6,127,449 | A | * | 10/2000 | Bissinger et al. | 523/109 |
| 6,127,450 | A | * | 10/2000 | Angeletakis | 523/116 |
| 6,201,038 | B1 | | 3/2001 | Waller et al. | |
| 6,383,279 | B1 | * | 5/2002 | Eckhardt et al. | 106/38.2 |
| 6,395,801 | B1 | * | 5/2002 | Bissinger et al. | 523/109 |
| 6,455,029 | B1 | * | 9/2002 | Angeletakis et al. | 424/49 |
| 6,552,104 | B1 | | 4/2003 | Hare | |
| 6,652,281 | B1 | * | 11/2003 | Eckhardt et al. | 433/219 |
| 6,762,242 | B1 | * | 7/2004 | Torto et al. | 524/588 |
| 6,765,036 | B2 | * | 7/2004 | Dede et al. | 522/15 |
| 6,779,656 | B2 | * | 8/2004 | Klettke et al. | 206/219 |
| 6,844,409 | B2 | * | 1/2005 | Angeletakis et al. | 526/279 |
| 6,867,246 | B2 | * | 3/2005 | Nowak et al. | 523/109 |
| 6,894,144 | B1 | * | 5/2005 | Zech et al. | 528/394 |
| 6,906,117 | B2 | * | 6/2005 | Nowak et al. | 523/109 |
| 6,919,386 | B2 | * | 7/2005 | Wanek et al. | 523/109 |
| 7,001,590 | B1 | * | 2/2006 | Angeletakis | 424/49 |
| 7,053,135 | B2 | | 5/2006 | Schaub et al. | |
| 7,060,769 | B2 | * | 6/2006 | Angeletakis | 526/171 |
| 7,060,770 | B2 | * | 6/2006 | Angeletakis | 526/171 |
| 7,097,456 | B1 | * | 8/2006 | Dede et al. | 433/226 |

(Continued)

FOREIGN PATENT DOCUMENTS

DE 1745810 1/1970

(Continued)

OTHER PUBLICATIONS

Geis-Gerstorfer J. et al., "Initial hydrophilicity of 15 type 3 impression materials during setting." IADR 2004 #1385. Rupp F., et al., "Hydrophilicity of elastomeric non-aqueous materials during setting." Dental Materials 21, 2005, 94-102).
International Search Report, PCT/US2007/074162, International Filing Date: Jul. 24, 2007, 5 pages.
ASTM D2849-69 Method C, 1980.
Noll, Walter, *Chemistry and Technology of Silicones*, pp. 447-452, 1968.
Polyethers Part I, Norman G. Gaylord, ed., pp. 147-150, 1963.
Polyethers Part I, Norman G. Gaylord, ed. pp. 231-237, 1963.
Silwet Surfactants, (1988) pp. 1-20.
Ucon Fluids & Lubricants (1955) Table of Contents.
Phillips, Ralph W., *Skinner's Science of Dental Materials*, 7th ed., 1973, p. 141.
*Ullman's Encyclopedia of Industrial Chemistry*, 5th Ed., vol. A24, pp. 65-66 and 69, 1993.
Brown, David, *Journal of Denistry*, vol. 1, pp. 265-274.

*Primary Examiner* — James Seidleck
*Assistant Examiner* — Peter A Salamon

(57) ABSTRACT

The invention relates to preparations based on polymerizable polyether materials and a fluidity improver and to the use thereof in producing dental materials, especially impression materials.

16 Claims, No Drawings

U.S. PATENT DOCUMENTS

| | | | |
|---|---|---|---|
| 7,173,097 B2 * | 2/2007 | Angeletakis | 526/171 |
| 7,235,602 B2 * | 6/2007 | Klettke et al. | 524/858 |
| 7,456,246 B2 * | 11/2008 | Kamohara et al. | 528/43 |
| 7,625,551 B2 * | 12/2009 | Angeletakis | 424/49 |
| 7,625,991 B2 * | 12/2009 | Angeletakis et al. | 528/29 |
| 7,799,846 B2 * | 9/2010 | Eckert et al. | 523/116 |
| 2002/0156149 A1 | 10/2002 | Schaub et al. | |
| 2003/0035899 A1 * | 2/2003 | Klettke et al. | 427/387 |
| 2003/0109596 A1 * | 6/2003 | Wanek et al. | 523/115 |
| 2003/0153726 A1 * | 8/2003 | Eckhardt et al. | 528/423 |
| 2003/0166737 A1 * | 9/2003 | Dede et al. | 522/7 |
| 2004/0014924 A1 * | 1/2004 | Nowak et al. | 528/28 |
| 2004/0152858 A1 * | 8/2004 | Kamohara et al. | 528/25 |
| 2004/0186202 A1 * | 9/2004 | Klettke et al. | 523/400 |
| 2005/0171233 A1 * | 8/2005 | Bublewitz et al. | 523/116 |
| 2005/0203207 A1 * | 9/2005 | Klettke et al. | 523/115 |
| 2005/0250871 A1 * | 11/2005 | Bublewitz et al. | 523/109 |
| 2006/0106127 A1 * | 5/2006 | Klettke et al. | 523/113 |
| 2006/0173091 A1 * | 8/2006 | Angeletakis | 523/109 |
| 2006/0247327 A1 * | 11/2006 | Klettke et al. | 523/109 |
| 2007/0173557 A1 * | 7/2007 | Bublewitz et al. | 523/109 |
| 2007/0197741 A1 * | 8/2007 | Angeletakis et al. | 525/446 |

FOREIGN PATENT DOCUMENTS

| | | |
|---|---|---|
| DE | 1544837 | 4/1970 |
| DE | 2515593 | 10/1975 |
| DE | 3245052 | 6/1984 |
| DE | 3246654 | 6/1984 |
| DE | 3728216 | 3/1988 |
| DE | 3741575 A1 | 6/1988 |
| DE | 3805482 | 8/1989 |
| DE | 4010281 | 4/1990 |
| DE | 3838587 | 5/1990 |
| DE | 4019249 | 1/1991 |
| DE | 4031759 A1 | 9/1992 |
| DE | 4119484 | 12/1992 |
| DE | 4129613 A1 | 11/1993 |
| DE | 4306997 A1 | 9/1994 |
| DE | 19719438 A1 | 11/1997 |
| DE | 19711514 A1 | 9/1998 |
| DE | 19740234 A1 | 3/1999 |
| DE | 19942459 A1 | 3/2001 |
| DE | 10001747 A1 | 7/2001 |
| DE | 10018918 A1 | 11/2001 |
| DE | 10026852 A1 | 12/2001 |
| DE | 10104079 A1 | 8/2002 |
| DE | 10244693 A1 | 4/2004 |
| EP | 0110429 A2 | 6/1984 |
| EP | 0173085 A2 | 3/1986 |
| EP | 0366977 A2 | 5/1990 |
| EP | 0 231420 B1 | 4/1991 |
| EP | 0421371 A2 | 4/1991 |
| EP | 0369394 B1 | 8/1993 |
| EP | 0480238 B1 | 7/1994 |
| EP | 0269071 B1 | 10/1995 |
| EP | 0268347 B2 | 2/1997 |
| EP | 0244478 B1 | 4/2000 |
| EP | 1426413 A1 | 6/2004 |
| EP | 1290998 B1 | 3/2005 |
| GB | 1509245 | 5/1978 |
| JP | 4293955 | 10/1992 |
| JP | 2004331738 A1 | 5/2003 |
| WO | 02/43670 A2 | 6/2002 |
| WO | 2004/058196 A1 | 7/2004 |

* cited by examiner

POLYETHER-BASED PREPARATIONS AND USE THEREOF

CROSS REFERENCE TO RELATED APPLICATIONS

This application is a national stage filing under 35 U.S.C. 371 of PCT/US2007/074162, filed Jul. 24, 2007, which claims priority to EP Patent Application Serial No. 06015830.0, filed Jul. 28, 2006.

BACKGROUND

The invention relates to preparations based on curable polyethers and to the use thereof in producing dental materials, especially impression materials.

Making an impression of the specific features inside the mouth of a patient using suitable impression materials is a prerequisite for the production of exactly fitting dentures, crowns and bridges, inlays and onlays. Amongst the known impression materials, the materials which are based on aziridino polyethers are outstanding, by virtue of their inherently hydrophilic nature and their flow properties in the cured state, as a result of which high-precision impressions are obtained.

Taking impressions of a dental situation in a patients mouth usually requires the employed impression material to allow for such high-precision impressions and many attempts have been made in order to improve the features of such impression materials. Most of these attempts, however, were directed to the improvement of the precision of the impression taken, e.g. by altering the curing time, the flow properties or the hydrophilicity of the impression materials.

EP 0 480 238 A1 relates to hydrophilic dental impression materials which cure by a polyaddition reaction.

WO 2004/058196 A1 relates to a dental impression material comprising a polyvinylsiloxane and a surfactant, wherein the surfactant imparts wettability to the composition, such that the material has a surface contact angle with water of less than about 10 degrees after about 15 seconds.

EP 0 268 347 A1 (corresponding to CA 1294946) relates to two-component dental impression materials based upon polyvinylsiloxane elastomers which include a catalyst paste preferably containing a hydrophilic surfactant.

U.S. Pat. No. 4,877,845 relates to curable composition comprising an unsaturated polyether having terminal alcanyl groups, a linear or branch siloxane-substituted polyether having terminal polyorganosiloxane residues and at least two SiH-groups in the molecule.

U.S. Pat. No. 5,849,812 relates to addition crosslinking polyether impression materials which can contain unbranched or branched siloxane-substituted polyethers.

In US 2003/109596 it is stated that the removability of a dental impression and the demouldability of the plaster model can be improved using polyether based preparations having a cyclic polyether content lower than 5.0 wt.-% and the use thereof.

WO 02/43670 relates to dental compounds with reduced temperature sensitivity. The components described contain a polyether part which has 10 to 250 methyl side-groups per 1,000 C- and O-atoms.

SUMMARY OF THE INVENTION

A disadvantage of the impression materials known from the prior art lies in the dissatisfactory handling behaviour of the uncured masses, which are supplied to the dentist in the form of separate pastes, usually a base paste and a catalyst paste. Especially when dealing with material of types 1, 2 or 3 (terminology according to ISO 4823:2000), mixing of base and catalyst paste often required either complicated motorized mixing gear or the use of high force, when trying to mix the pastes with manually driven gear. Sometimes, the personnel in a dentists practice has difficulties to provide the necessary force for manually mixing the pastes.

Since the use of a manual mixing gear is found to be convenient, it would be desirable to have preparations based on curable polyethers for producing dental materials, especially impression materials, which are provided in the form of two or more components, especially in the form of a base paste and a catalyst paste, which can be mixed by common manual dispensers, such as dispensers for two-component double syringes. There is accordingly a need for impression materials which can be dispensed by manually driven dispensers.

A material adapted to be used with a manually driven dispenser, however, should not exhibit disadvantages with regard to allowing for high precision impressions from a dental situation in a patients mouth. There has thus furthermore been a need for impression materials which, despite being able to be dispensed by manually driven dispensers, have acceptable properties in the uncured state as well as acceptable mechanical properties and good long-term stability.

The problem is solved by preparations, and dental materials produced therefrom, as are provided by the present invention.

The invention relates to a dental impression material comprising
polymerizable polyether material which is selected from the group consisting of
a) polyethers with at least one aziridino group,
b) polyethers with at least one olefinically unsaturated group and a compound with at least one SiH group and
c) polyethers with at least one olefinically unsaturated group and at least one SiH group and
d) polyethers with at least one alkoxysilyl group;
e) polyethers with at least one olefinically unsaturated group and a metal carbene
and about 0.1 to about 15% by weight of a random copolyether of ethyleneoxide and at least one more alkyleneoxide which is not ethylene oxide, the copolymer comprising at least about 50% of structural elements from ethylene oxide as a fluidity improver.

It can be preferred, if the fluidity improver is not a tenside and it has in some instances been found to be advantageous if the fluidity improver has a predominantly linear polymer backbone. The fluidity improver can have a $M_w$ of about 100 to less than about 3800. In another embodiment of the invention, the fluidity improver is a linear random copolymer with a molecular weight of at least about 200 and at least 1 OH endgroup.

It can further be advantageous, if the fluidity improver has one or more of the following features:
the fluidity improver comprises repeating groups based on ethylene oxide and propylene oxide or butylene oxide or their mixture,
the fluidity improver is a linear random copolymer with one or two $C_1$-$C_4$-alkyl ether endgroups or one or two $C_1$-$C_4$-alkyl ester endgroups or one $C_1$-$C_4$-alkyl ether endgroup and one $C_1$-$C_4$-alkyl ester endgroup,
the fluidity improver is a linear random copolymer from ethyleneoxide and propyleneoxide or ethyleneoxide and butyleneoxide, the fluidity improver is a liquid at 23° C. and 101 325 Pa.

A dental impression material according to the invention can preferably comprise the fluidity improver in an amount of about 0.5 to about 12% by weight with respect to the whole composition.

The initial contact angle of a dental material comprising the fluidity improver is preferably at least about 8% less than the initial contact angle of the same dental material without the fluidity improver.

In one embodiment, the dental impression material according to the invention preferably comprises at least one polyether with two or more aziridino groups and the polyether-backbone is a copolymer of ethylene oxide and propylene oxide or ethyleneoxide and butylene oxide. It can be preferred, if in a dental impression material according to the invention, the polyether with two or more aziridino groups has a molecular weight $M_w$ of more than about 3000 or the impression material comprises at least one polyether with two or more olefinically unsaturated groups and the polyether-backbone is a copolymer of ethylene oxide and propylene oxide or ethyleneoxide and butylene oxide.

In another embodiment, the dental impression material according to the invention comprises at least one polyether with at least one olefinically unsaturated group and at least one compound with at least one SiH group or a polyether with at least one olefinically unsaturated group and at least one SiH group and the polyether backbone of at least one of the polyethers has a polymer back bone which is a copolymer of ethylene oxide and propylene oxide or ethyleneoxide and butylene oxide.

A dental impression material according to the invention can contain one or more adjuvants selected from the group consisting of catalysts, plasticizers, fillers, softeners, dyes, pigments, solvents, disinfectants, thinners, flavorants, odorants, theological additives, emulsifiers or stabilizers.

It can be preferred, if a dental impression material according to the invention is supplied in at least 2 separate components. If the dental impression material is supplied in 2 separate components, it is preferred, if one of component is a base paste and one component is a catalyst paste, wherein the base paste contains at least one polymerizable polyether material which is selected from the group consisting of
a) polyethers with at least one aziridino group,
b) polyethers with at least one olefinically unsaturated group and a compound with at least one SiH group and
c) polyethers with at least one olefinically unsaturated group and at least one SiH group and
d) polyethers with at least one alkoxysilyl group;
e) polyethers with at least one olefinically unsaturated group
and the catalyst paste contains at least one initiator or catalyst or both for initiating or catalyzing the polymerization of the at least one polymerizable polyether material or both.

If the dental material according to the invention is present in 2 components, one of which is a base paste and one of which is a catalyst paste, the fluidity improver is contained in the base paste or in the catalyst paste or in the base paste and in the catalyst paste. The base paste preferably comprises about 40 to about 70% by weight of at least one polymerizable polyether material, about 0.11 to about 60% by weight of a fluidity improver or of a mixture of two or more fluidity improvers and 0 to about 59.89% by weight of adjuvants and the base paste is mixed with the catalyst paste in a ratio of about 1:9 to about 9:1. The catalyst paste preferably comprises about 0.01 to about 30% by weight of an initiator or a catalyst or both, 0 to about 60% by weight of a filler or of a mixture of two or more fillers, 0 to about 99.99% by weight of a fluidity improver or a mixture of two or more fluidity improvers and 0 to about 99.99% by weight of adjuvants and the base paste is mixed with the catalyst paste in a ratio of about 1:9 to about 9:1, preferably in a ratio of about 1:1 to about 5:1.

The invention also relates to a cured dental impression material obtainable by curing a dental impression material according to the invention.

A further aspect of the invention relates to a method for obtaining a dental impression material, wherein
A) a polymerizable polyether material which is selected from the group consisting of
a) polyethers with at least one aziridino group,
b) polyethers with at least one olefinically unsaturated group and a compound with at least one SiH group and
c) polyethers with at least one olefinically unsaturated group and at least one SiH group and
d) polyethers with at least one alkoxysilyl group;
e) polyethers with at least one olefinically unsaturated group and a metal carbene and
B) about 0.01 to about 15% by weight of a random copolyether of ethyleneoxide and at least one more alkyleneoxide which is not ethylene oxide, the copolymer comprising at least about 50% of structural elements from ethylene oxide as a fluidity improver, and
optionally one or more adjuvants selected from the group consisting of catalysts, plasticizers, fillers, softeners, dyes, pigments, solvents, disinfectants, thinners, flavorants, odorants, rheological additives, emulsifiers or stabilizers are mixed.

In another embodiment of the invention, the constituents are supplied in a base paste and a catalyst paste prior to mixing or are mixed by a manually driven dispenser or both.

In a further aspect, the invention relates to a method for obtaining a dental impression of a mammal or a human being (patient), wherein a dental impression material according to the invention or a dental impression material obtained according to the invention administered to the site in the patients mouth to be represented in the dental impression, at least partially cured and a dental impression is retrieved from the patients mouth. The impression material is preferably left in contact with the site in the patients mouth to be represented for about 1 to about 10 minutes and is rinsed or disinfected or both after retrieval from the patients mouth.

The invention also relates to a method for the preparation of a plaster model of a dental situation in the mouth of a mammal or a human being (patient), wherein a dental impression is taken according to the invention and the dental impression is filled with plaster which is hardened and retrieved from the dental impression.

Another aspect of the invention is the use of a dental impression material comprising
polymerizable polyether material which is selected from the group consisting of
a) polyethers with at least one aziridino group,
b) polyethers with at least one olefinically unsaturated group and a compound with at least one SiH group and
c) polyethers with at least one olefinically unsaturated group and at least one SiH group and
d) polyethers with at least one alkoxysilyl group;
e) polyethers with at least one olefinically unsaturated group and a metal carbene
and about 0.1 to about 15% by weight of a random copolyether of ethyleneoxide and at least one more alkyleneoxide which is not ethylene oxide, the copolymer comprising at least about 50% of structural elements from ethylene oxide as a fluidity improver, for taking dental impressions from the mouth of a mammal or a human being.

The invention is now described in more detail.

DETAILED DESCRIPTION OF THE INVENTION

In the context of the present text, a "composition" is understood to be a mixture of two or more compounds. In the context of the present text, the terms "polymerizable" and "curable" are used interchangeable, both referring to the formation of material with a higher molecular weight, by a polymerization reaction.

A "polymerization reaction" according to the present text can generally be a polyaddition reaction or a polycondensation reaction or a metathesis reaction.

The term "molecular weight" refers herein to the weight average of the molecular weight, as is conventionally determined for the individual classes of polymers by gel permeation chromatography (GPC) against a standard of defined molecular weight. Suitable measurement methods are known to the person skilled in the art.

Furthermore, the determination of the molecular weights and the molecular weight distribution of polymeric polyols can be carried out, for example, by means of end group determination, for example by nuclear magnetic resonance (NMR) methods. Also suitable for the determination of the molecular weights and the molecular weight distribution of polymeric polyols is the determination of the hydroxyl value, as is described, for example, in Houben-Weyl "Methoden der organischen Chemie", 14/2, p. 17, Georg Thieme Verlag, Stuttgart, 1963. Also suitable is the procedure described in ASTM D2849—Method C.

An especially suitable method of determining the molecular weight ($M_w$ and $M_n$) and molecular weight distribution of organic diols can be carried out, for example, by means of GPC using a column combination PSS SDV 10,000 Å+PSS SDV 500 Å+PSS SDV 100 Å with column dimensions of 8×300 mm and a particle size of 5 µm. As a pre-column there is used a PSS SDV 100 Å having column dimensions of 8×50 mm and a particle size of 10 µm. THF stabilised with 200 ppm of Ionol, at a flow rate of 1.0 ml/min, is especially suitable as the mobile phase. As the detector there is used a refractive index (RI) detector; the injection volume for the samples (1% w/w weighed into the mobile phase) is 100 µl. As the standard solution there is used a polystyrene standard series (0.1% w/w weighed into the mobile phase). The evaluation is carried out according to the principle of relative GPC using an automatic evaluation module (TurboSEC Software) by means of comparison of the volumes of sample eluted with the volumes of the polystyrene standard series eluted. $M_n$, $M_w$ and polydispersity are evaluated.

A "polymerizable polyether" material according to the invention can be any material comprising at least 2 ether linkages in the molecule. Generally, any oligomeric or polymeric material with the required amount of ether groups can be used for the oligomeric or polymeric backbone of the polymerizable polyether material according to the invention.

In one embodiment the polymerizable polyether has a linear backbone having no side chains pending from the backbone, especially no non-reactive side chains including methyl, ethyl or propyl groups. That is, the backbone of the polymerizable polyether mainly comprises groups such as —$CH_2$— and hetero atoms including N, O and S. The backbone is defined as the part of the polymerizable polyether which bears the polymerizable groups.

The polymeric backbone of the polymerizable polyether material according to the invention can be a backbone obtained by polycondensation and will be called a polycondensation product hereinafter. In principle all polymers which can be prepared by polyaddition or polycondensation methods are suitable for the present invention as polycondensation products, provided that they meet the requirements of the composition with respect to their preferred use as dental materials. Suitable polycondensation products are, for example, polyesters, polyacetals or polysiloxanes.

Among the known, variously constituted, polyesters, those that are obtainable by polycondensation of dicarboxylic acids with diols or by polycondensation of oxycarboxylic acids and that have a substantially linear structure are especially suitable for preparation of the starting materials. The concomitant use of small amounts of tri- or tetra-functional alcohols or carboxylic acids during the polycondensation is possible and, in many cases, even advantageous for the mechanical properties of the compositions obtainable from the polyesters with respect to the use thereof as dental materials.

A large number of polyols can be used as polyols for the preparation of the above-mentioned polyesters. They are, for example, aliphatic alcohols having from 2 to 4 OH groups per molecule. The OH groups may be either primary or secondary. Suitable aliphatic alcohols include, for example, ethylene glycol, propylene glycol, 1,4-butanediol, 1,5-pentanediol, 1,6-hexanediol, 1,7-heptanediol, 1,8-octanediol and higher homologues or isomers thereof, as the skilled person will obtain by stepwise extension of the hydrocarbon chain in steps of one $CH_2$ group or by introducing branches into the carbon chain. Also suitable are higher-functional alcohols such as, for example, glycerol, trimethylolpropane, pentaerythritol and also oligomeric ethers of the mentioned substances either alone or from a mixture of two or more of the mentioned ethers together.

The reaction products of low-molecular-weight polyfunctional alcohols with alkylene oxides, so-called polyethers, may also be used as polyols. The alkylene oxides preferably have from 2 to 4 carbon atoms. There are suitable, for example, the reaction products of ethylene glycol, propylene glycol, butanediol or hexanediol isomers with ethylene oxide, propylene oxide or butylene oxide, or mixtures of two or more thereof Furthermore, the reaction products of polyfunctional alcohols such as glycerol, trimethylolethane or trimethylolpropane, pentaerythritol or sugar alcohols, or mixtures of two or more thereof, with the mentioned alkylene oxides, forming polyether polyols are also suitable.

Appropriate polyethers are brought about in a manner known to the person skilled in the art by reaction of the starting compound having a reactive hydrogen atom with alkylene oxides, for example ethylene oxide, propylene oxide, butylene oxide, styrene oxide, tetrahydrofuran or epichlorohydrin or mixtures of two or more thereof.

Suitable starting compounds are, for example, water, ethylene glycol, 1,2- or 1,3-propylene glycol, 1,4- or 1,3-butylene glycol, 1,6-hexanediol, 1,8-octanediol, neopentyl glycol, 1,4-hydroxymethylcyclohexane, 2-methyl-1,3-propanediol, glycerol, trimethylolpropane, 1,2,6-hexanetriol, 1,2,4-butanetriol, trimethylolethane, pentaerythritol, mannitol, sorbitol, or mixtures of two or more thereof.

For the preparation of appropriate polyesters there are suitable, for example, succinic acid, adipic acid, suberic acid, azelaic acid, sebacic acid, phthalic acid, isophthalic acid, terephthalic acid, trimellitic acid, phthalic anhydride, tetrahydrophthalic anhydride, hexahydrophthalic anhydride, tetrachlorophthalic anhydride, endomethylene-tetrahydrophthalic anhydride, glutaric anhydride, maleic acid, maleic anhydride, fumaric acid, dimer fatty acid or trimer fatty acid or mixtures of two or more thereof. Where appropriate, minor amounts of monofunctional fatty acids may be present in the reaction mixture. Likewise suitable are unsaturated dicarboxylic acids such as maleic acid or fumaric acid and aromatic dicarboxylic acids, for example the phthalic acid isomers such as phthalic acid, isophthalic acid or terephthalic acid. As tricarboxylic acids there are suitable, for example, citric acid or trimellitic acid. The mentioned acids may be used singly or in the form of mixtures of two or more thereof.

The polyesters may, where appropriate, have a small proportion of carboxyl end groups. Polyesters obtainable from lactones, for example ε-caprolactone, or hydroxycarboxylic acids, for example ω-hydroxycaproic acid, may also be used.

Polyacetals are also suitable as polyol condensation products. Polyacetals are understood to be compounds such as are obtainable from glycols, for example diethylene glycol or hexanediol or a mixture thereof, with formaldehyde. Polyacetals which can be used in the context of the invention may also be obtained by the polymerisation of cyclic acetals.

As polysiloxanes there are suitable, in principle, all polysiloxanes which meet the requirements in terms of material properties with regard to the preferred use as dental materials. Special preference is given in the context of the present invention, however, to, for example, the polysiloxane basic structures of the aziridino-group-carrying polysiloxanes described in DE 100 26 852 A1 from p. 2, line 55 to p. 8, line 20 (corresponding to U.S. Pat. No. 6,867,246). The disclosure of the mentioned publication is regarded as part of the disclosure of the present text.

As polyaddition products there are suitable in the context of the present invention, in principle, all polymers which can be prepared by polyaddition methods provided that they meet the requirements of the composition with regard to the preferred use thereof as dental materials. Suitable polyaddition products are, for example, polyurethanes or polyethers.

As polyurethanes there are suitable, in principle, all polymers which can be prepared by the reaction of polyols or polycarboxylic acids and isocyanates. Appropriate preparation methods will be known to the person skilled in the art; suitable polyols have already been described in the context of the present text as starting materials for the preparation of the above-mentioned polyesters.

In the context of a preferred embodiment of the present invention, there are used, as constituents of the compositions according to the invention, polyaddition products, these preferably being polyethers.

As polyethers there are suitable, in principle, all polyether compounds which meet the requirements in terms of material properties with regard to the preferred use as dental materials. Suitable polyethers and processes for their preparation are described, for example, hereinbefore in the context of the present text. Especially suitable are polyether compounds as are obtainable by polyaddition of ethylene oxide, 1,2-propylene oxide, 1,2-butylene oxide or tetrahydrofurane or of mixtures of two or more of the mentioned compounds with the aid of a suitable starting compound and a suitable catalyst.

However, in the context of the present invention, polyether compounds having a constituent of at least one repeating unit derived from 1,2-propylene glycol in the polyether chain are especially suitable. Accordingly, as basic polyether frameworks for the aziridino-group-carrying polymers contained in a composition according to the invention there are suitable, for example, polypropylene glycol or ethylene glycol/propylene glycol copolymers or tetrahydrofuran/propylene glycol copolymers or tetrahydrofuran/ethylene glycol copolymers or mixtures of two or more thereof, especially polypropylene glycol or ethylene glycol/propylene glycol copolymers or tetrahydrofuran/ethylene glycol copolymers.

For example, polyether polyols which are prepared by copolymerisation of tetrahydrofuran and ethylene oxide in a molar ratio of from about 10:1 to about 1:1, preferably to about 3:1, in the presence of strong acids, for example boron fluoride etherates, are suitable.

The polyether polyols which can be used for preparation of a polymerizable polyether material can have, on average, at least 2 hydroxyl groups but may also have up to about 20 hydroxyl groups per molecule, for example on average up to about 3, 4, 5, 8, 10 or 15 hydroxyl groups.

The molecular weights ($M_n$) of the polyether polyols are usually in the range from about 600 to about 20,000 g/mol, preferably in the range from about 1,000 to about 10,000 g/mol.

The distribution of the structural units in the polymer which are based on different monomers can be organised randomly or in blocks.

Furthermore, suitable polyethers are described in DE PS 1 745 810 (corresponding to U.S. Pat. No. 3,453,242), the disclosure of which in that respect is regarded as part of the disclosure of the present text.

The polymerizable polyether material to be used according to the invention can generally comprise any functional group which can polymerize by a polymerization reaction as defined above. It can be preferred, if an impression material according to the invention comprises a polyether compound which is curable, e.g., via cationic ring-opening polymerization with sulfonuim salts as the initiator(s), via condensation reaction with acids and/or salts of acids as the as the initiator(s), via hydrosilylation reaction with platinum compounds as the initiator(s) or via ring-opening metathesis reaction with metal carbenes as the initiator(s).

Aziridino Polyethers

In a further aspect of the invention, the polymerizable polyethers carry, on average, at least 2 aziridino groups (hereinafter called: aziridino polyethers).

The term "on average" is to be interpreted in the context of the present text such, that a mixture of a large number of compounds of aziridino polyethers may comprise both compounds having less than 2 aziridino groups and also compounds having more than 2 aziridino groups although, when seen over the entirety of the compounds of component Z1, the average functionality of all molecules is, with respect to aziridino groups, 2 or more.

All mentioned types of polyaddition or polycondensation products can be provided with aziridino groups by means of any desired subsequent reactions known to the person skilled in the art. For example, it is possible first to introduce, into an appropriate polymer, substituents which are in turn capable of reacting with suitable aziridine derivatives.

Suitable possible methods for providing the polymers with aziridino groups are mentioned, by way of example, in DE PS 1 745 810 or DE 100 26 852 A1; reference is expressly made to the mentioned publications, and the disclosure thereof with respect to functionalising polymers with aziridino groups is understood to be part of the disclosure of the present text.

Suitable aziridino polyethers can carry the aziridino groups terminally or laterally, or terminally and laterally, but preferably terminally.

The aziridino polyethers should preferably have a dynamic viscosity η of from about 10 to about 500 Pa*s, especially from about 15 to about 300 Pa*s (23° C., measured with a rotary viscometer of the CVO 120 HR type from the company Bohlin Instruments GmbH Pforzheim at 23° C., plate-plate geometry, plate diameter: 20 mm, or plate-cone geometry, shear rate 20 s$^{-1}$). A preferred viscosity range is from about 20 to about 180 Pa*s at 23° C.

The aziridino equivalent should be from about 250 to about 25,000 g/equivalent, especially from about 400 to about 10,000 g/equivalent.

A polymerizable polyether which can be used in accordance with the invention may comprise only one type of aziridino polymer. It is, however, likewise possible that it comprises two or more different types of aziridino polymers, for example 3, 4 or 5 different types.

A "type of polymer" is understood, in the context of the present invention, to be a polymer as results from the polyaddition or polycondensation or metathesis reaction of selected monomers under the selected reaction conditions. A type of polymer can accordingly include polymer molecules of differing chemical constitution and differing molecular weight, depending on the reaction conditions selected. However, two reactions carried out using identical monomer compositions under identical reaction conditions always result, in accordance with the invention, in identical types of polymer. Two reactions which are carried out using identical monomers but under different reaction conditions may result in identical types of polymer but need not do so. An important factor therein is whether there are identifiable differences—in terms of chemical constitution, molecular weight and further parameters which can be determined—that are of relevance to the material properties. Two reactions which are carried out using different monomer compositions always result, in accordance with the invention, in different types of polymers.

The above-described aziridino polymers can usually be used in the form in which they are obtained in the course of preparation, but they may also be purified in order to obtain especially lightly coloured and high-quality products. For that purpose there come into consideration the customary methods, for example filtration, optionally in solution, over kieselguhr, aluminium oxide, treatment with ion exchangers, washing of the solutions in organic solvents using water, aqueous alcohol, salt solutions and the like, and also optionally repeated reprecipitation, for example from aromatic solvents or alcohols. Furthermore, a purification effect can be obtained by fractionation in the usual manner. In addition, products having a more uniform molecular weight are obtainable as a result.

A dental material according to the invention preferably comprises at least one aziridino polymer which has, as its basic framework, a polyether, preferably a polyether based on polytetrahydrofuran (poly-THF) or a propylene glycol/ethylene glycol copolymer or an ethylene glycol/tetrahydrofuran copolymer, irrespective of the manner of preparation.

Further polyaziridino compounds suitable are mentioned, for example, in the Offenlegungsschrift DE 15 44 837, p. 3-p. 14 (corresponding to U.S. Pat. No. 3,453,242).

Trialkylsulfonium salts as are described in, for example, U.S. Pat. No. 4,167,618 (e.g.: column 2, line 36-column 4, line 32 and Examples) are especially suitable as initiator substances. The mentioned trialkylsulfonium salts are understood as being part of the disclosure of the present text.

In the patent specification DE 914 325, the use of oxonium, ammonium and sulfonium salts as initiator substances is proposed (e.g.: p. 2, line 77-p. 3, line 100 and Examples), the initiator substances mentioned therein likewise being considered part of the disclosure of the present text.

In the patent application US 2003/0153726, initiators are described which impart just a low degree of acidity to the catalyst component and which make possible a readily adjusted, relatively long processing time after mixing of the basic component and catalyst component has been carried out. Reference is expressly made also to the compounds mentioned therein and the initiator substances mentioned therein are likewise considered part of the disclosure of the present text.

The initiator compounds mentioned in U.S. Pat. No. 4,176,618 are also suitable. The disclosure of that publication in respect of initiator substances is considered part of the disclosure of the present text.

Initiator systems of that type are suitable for curing the basic components according to the invention at the requisite rate. By virtue of their use, the desired properties of the resilient solid body can be achieved.

U.S. Pat. No. 6,894,144 A1 describes elastomeric materials having an improved catalyst component which are distinguished by increased extensibility. In accordance with that invention, boric acid complexes are used as initiators. Those initiators have likewise been found to be suitable for the curing of N-alkylaziridino polymers and can be used in the context of the present invention.

In the context of the present invention, the following initiator compounds are preferably used: the zinc salt of p-toluenesulfonic acid, β-(S-lauryl-S-ethylsulfonium)butyronitrile tetrafluoroborate, dodecylbenzenesulfonic acid zinc salt, β-(S-lauryl-S-ethylsulfonium)-β-phenylacrylic acid butyl ester tetrafluoroborate.

Polyethers Polymerizable by ROMP

The dental material according to the invention can also comprise a material which is polymerizable by ring-opening metathesis polymerization (ROMP) as a polymerizable polyether. Such a material is preferably comprising at least one polyether compound that is polymerizable by ring opening metathesis polymerization (ROMP) and at least one initiator for initiating the ROMP.

In a preferred embodiment, a composition according to the invention contains a monomer which is polymerizable by ROMP and comprises at least one C—C double bond in a cyclic structure.

Generally, all types of polyether compounds can be part of the dental material according to the invention which have one moiety or preferably two or more moieties that can be polymerized by ROMP.

Generally, suitable monomers can follow the general formula B-An wherein A is a moiety polymerizable by ROMP preferably cyclobutenyl, cyclopentenyl, cyclooctenyl or bicyclic ring systems like the often preferred norbornenyl and 7-oxa-norbornenyl groups, B is an polyether based organic or silicon-organic backbone with 1 to about 100, e.g., 1 to about 10 or 1 to about 5 or 1 to about 4 moieties polymerizable by ROMP, e.g., 2 or 3 moieties polymerizable by ROMP, are attached, n being about 1 to about 100. The composition according to the invention can contain only one type of monomers according to the general formula B-$A_n$. It is also possible that a composition according to the invention contains two or more different types of monomers according to the general formula B-$A_n$. The composition according to the invention preferably contains at least one type of monomer according to the general formula B-$A_n$, which has one or preferably two olefinically unsaturated double bonds which are curable by ROMP.

The bicyclic ring systems which can be used according to the invention preferably have no exocyclic C—C double bonds like (meth)acrylate groups so that the curing of the compositions takes place at least predominantly by ring-opening metathesis polymerization (ROMP). Furthermore, it can in some instances be advantageous if the bicyclic ring system also contains no vinyl or allyl groups as these sometimes may function as a chain-terminating agent during ROMP. Despite that, however, addition of chain terminating agents in order to regulate polymerization can be preferred.

The compositions according to the invention can contain bicyclic ring systems with 1 to 2 endocyclic double bonds. Carbocyclic ring systems are particularly preferred as well as oxygen-substituted ring systems.

Carbocyclic and heterocyclic bicyclo[x.y.z.]hydrocarbons with noticeable ring strain may often be particularly suitable, when x, y and z have values from 1 to 6. x is equal to about 2, y is equal to about 2 and z equal to 1.

Preferred representatives of this composition class are derivatives of bicyclo[2.2.1]heptene or 7-Oxa-bicyclo[2.2.1] heptene in particular those with unsaturation in 5-position and substitution in 2- or 2,3-position to the ring. Substituents in 2- or 2,3-position to the ring are preferably carbon- silicon- or oxygen-functional and connect to an unreactive residue or to an organic or metalorganic spacer bridging between two, three, four or more ROM-polymerizable groups.

Polyethers Crosslinking by Hydrosilylation

A dental material according to the invention can also contain an addition crosslinking material as a polymerizable polyether material, which is based upon
(a) at least one polyether which has at least two optionally substituted vinyl and/or allyl end-groups,
(b) an SiH component,
(c) at least one platinum catalyst, and optionally
(d) usual additives and optionally
(e) an organopolysiloxane with at least two alkenyl groups.

This material can be provided in a two-component form, in which the platinum catalyst (c) optionally together with the component (e) as a paste base in a so-called catalyst paste has an acceptable long-term storage stability, and in which separation of the polyether (a) and of the platinum catalyst (c) can take place.

In the preferred two-component version of the dental impression material according to the invention, components (a) and (b) are present in a so-called base paste, whereas components (c) and optionally (e) are present in the catalyst paste. It is, however, also conceivable for at least part of the optional component (e) to be present in the base paste or for at least part of component (a) to be present in the catalyst paste. However, the impression material according to the invention can also be constituted in such a way that all the components (a), (b), (c) and optionally (e) are present spatially separated. Furthermore, all three-component versions in which the components (b) and (c) are present spatially separated are also conceivable. The optionally present usual additives according to component (d) can be added to any other component or distributed over it.

The di- or polyallyl ethers of polyether di- or polyols can for example be used as unsaturated polyethers (a). The polymers of ethylene and propylene oxide, copolymers of ethylene and propylene oxide and copolymers of ethylene oxide and tetrahydrofuran can for example be used as the polyether middle section. The polyetherdiols obtained from this can then be reacted e.g. with allyl or also vinyl chloride in a manner known per se to give the unsaturated polyethers (a). The unsaturated polyethers preferably have average molecular weights of about 1000-about 20,000, particularly preferably of about 1500-about 10,000 quite particularly preferably of about 2000-about 7000. Suitable unsaturated polyethers are described in the afore-mentioned DE-A-37 41 575, the disclosure of which in this respect is to be included here.

Component (b) of the dental impression material as described above is a hydrocarbon or polyether compound, substituted by siloxane radicals, having at least 2 SiH groups in the molecule. The structure and method of production of these compounds are described inter alia in DE-A-38 38 587 (corresponding to U.S. Pat. No. 5,086,148) and, DE-A-37 41 575 (corresponding to U.S. Pat. No. 4,877,854). The disclosure of these publications in this respect is to be included here. Preferred components (b) are the SiH components described in DE-A 38 38 587 (corresponding to U.S. Pat. No. 5,086, 148), which are characterized in that they are obtainable by reacting an at least bifunctional allyl or vinyl hydrocarbon compound, the hydrocarbon radical of which, without taking into account that allyl or vinyl groups and optionally present alkylene ether groups, has about 6-about 30 C atoms and contains at least one aromatically unsaturated, heterocyclic or cycloaliphatic ring, with at least one mol per vinyl or allyl group of an at least bifunctional SiH compound of the formulae I or II.

Fluidity Improvers

A dental impression material according to the invention comprises about 0.1 to about 15% by weight of a random copolyether of ethylene oxide and at least one more alkyleneoxide which is not ethylene oxide, as a fluidity improver. The copolymer comprises at least about 50% of structural elements from ethylene oxide.

The term "random" in the context of the present invention relates to a copolymer comprising at least two different types of structural elements from different monomers which are randomly distributed over the polymer backbone or at least a part of the polymer backbone comprising two or more of such structural elements. A random copolymer can often be described as a copolymer in which the succession of structural elements coming from different monomers exhibits a distribution scheme between an alternating copolymer, in which such structural elements are following upon each other in an alternating manner, and a block copolymer, in which structural elements coming from a certain type of monomer form building blocks of two or more of such structural elements, which building blocks, in turn, exhibit an alternating succession in the polymer backbone.

Fluidity improvers according to the invention, can comprise structural elements coming from two or more monomers, while at least one of the monomers the structural elements in the polymer backbone are based on is ethylene oxide and the weight percentage of such structural elements with regard to the fluidity improver must be at least about 40% by weight.

As a result of the polymer backbone of the fluidity improver being a random copolymer, the polymer backbone can comprise random structural elements which show a block-like succession of structural elements. However, it can be advantageous if a fluidity improver according to the invention does not have block like arrangements of structural elements which impart a tensidic behaviour on the fluidity improver, i.e. the fluidity improver is not a tenside.

It can further be preferred, if a fluidity improver does not have a hydrophobic and hydrophilic part of the molecule which are clearly separated from each other in order to form a tensidic structure according to the definition given in Römpp Chemielexikon, 1995. It can further be preferred, if a fluidity improver does not exhibit oriented adsorption to interfaces or does not aggregate to form micelles or does not form lyotropic phases or a combination of two or more of these feature. In another embodiment, a fluidity improver according to the invention has a predominantly linear polymer backbone. It can further be preferred, if the molecular weight $M_w$ of the fluidity improver is in a range of about 100 to less than about 3800, or in a range of about 150 to about 3400 or in a range of about 200 to about 3000 or in the range of about 500 to about 2000 or in a range of about 500 to about 1900.

A fluidity improver according to the invention can have 0, 1, 2 or more OH-end groups, depending on the type of oligomeric or polymeric backbone and the linear or branched nature of the backbone. It can be advantageous, if a fluidity improver is used which has 0, 1 or 2 OH-end groups, preferably 0 or 1 OH-end groups.

A fluidity improver according to the invention can have an oligomeric or polymeric backbone with structural elements coming from different types of polymerizations. A fluidity improver can have structural elements in the polymer backbone which come from a polycondensation reaction, i.e. a polyester structure, and from a poly addition reaction, e.g. a polyether structure. It can be preferred if a fluidity improver is used as part of the dental impression materials which has a polyether backbone.

In another aspect of the invention a fluidity improver can be used which comprises structural elements in the polymer backbone which are based on ethylene oxide and propylene oxide or butylenes oxide or their mixture. The amount of ethylene oxide should exceed about 30% by weight and is can be in a range of about 35 to about 80 or 40 to about 60% by weight.

In a further-embodiment of the invention, a fluidity improver is used which has a polymer backbone comprising structural elements based on ethylene oxide and propylene oxide.

A fluidity improver in a dental material according to the invention can preferably have 1 or 2 $C_1$-$C_4$-alkyl ether end groups or 1 or 2 $C_1$-$C_4$-alkyl ester end groups or 1 $C_1$-$C_4$ alkyl ether end group and 1 $C_1$-$C_4$ alkyl ester end group.

Thus, according to a preferred embodiment, the fluidity improver of the invention does not comprise groups, which are reactive with the polymerizable polyether material. However, according to another embodiment of the invention, the fluidity improver can comprise groups, which are reactive with the polymerizable polyether material, e.g. unsaturated groups like vinyl or allyl groups.

While generally a fluidity improver can be used which is in the solid or in the fluid state, it has in some instances shown to be advantageous if a fluidity improver is used which is a liquid at 23° C. and 101.325 Pa of pressure.

While the fluidity improver is useful in an amount of about 0.1 to about 15% by weight in a dental impression material according to the invention, it can be advantageous to use the fluidity improver in an amount of about 0.5 to about 12% by weight or about 1 to about 8% by weight. The fluidity improver can be part of a catalyst paste or can be part of a base paste or can be part of both, if the material is offered in a two-component form consisting of a base, and a catalyst paste. It can, however, be preferred, if the fluidity improver is used as part of the base paste only. In this case, the amount of fluidity improver in the base paste can be in arrange of about 0.5 to about 30% by weight, preferably in a range of about 1 to about 20 or about 5 to about 15% by weight.

According to another embodiment of the invention, the base paste of the dental impression material comprises the fluidity improver together with plasticisers including triacyl glycerides described below. Without wishing to be bound to a certain theory it is believed that this combination of components in the base paste may help to further reduce the extrusion forces. In a further embodiment of the invention, the base paste is essentially free of softeners or plasticisers having a molecular weight below 500.

One of the prerequisites of a fluidity improver according to the invention is that it preferably should not result in worse material properties, e.g. with regard to the initial contact angle of the dental material after mixing the components.

Examples of useful fluidity improvers, which are commercially available, are random co-polymers from ethylene oxide and propylene oxide like Acclaime 3201 (Lyondell) or Breox 50 A 20, Breox 50 A 50, Breox 50 A 75, Breox 50 A 140, Breox 50 A 225, Breox 50 A 380, Breox 50 A 480, Breox 50 A 680, Breox 50 A 1000, Breox 75 W 270, Breox 75 W 2050, Breox 75 W 18000, Breox 75 W 30000, Breox 75 W 55000 (Laporte).

Further examples of useful fluidity improvers are polyethylene glycol monoalkyl ethers, especially polyethylene glycol monomethyl ethers, like PEG-350 monomethyl ether (Fluka), Pluriol A 350 E (BASF), Pluriol A 500E (BASF), Pluriol A 750 E (BASF), Pluriol A 1000 E (BASF), Pluriol A 2000 E (BASF), PEG-550 monomethyl ether (Fluka).

Adjuvants

A dental impression composition according to the invention can comprise one or more adjuvants (also hereinafter called additives) selected from the group consisting of catalysts, plasticizers, fillers, softeners, dyes, pigments, solvents, disinfectants, thinners, flavorants, odorants, theological additives, emulsifiers or stabilizers Suitable additives are, for example, compounds that bring about plasticising of the cured dental material compositions. Such compounds can be both typical plasticisers as are also provided for other polymer systems and also esters of polycarboxylic acids, polyaromatic compounds and sulfonic acid esters or compounds which, besides the plasticising, also bring about other effects such as a surfactant action, an increase in structural strength and an improvement in flow behaviour.

Typical plasticisers are, for example, compounds of the ester type such as $C_{12}$- to $C_{15}$-alkyl lactates, ethyl or butyl esters of citric acid or of acetylcitric acid, phthalic acid esters of relatively long, branched alcohols such as bis(2-ethylhexyl)phthalate or phthalic acid polyester, $C_2$- to $C_{22}$-dialkyl esters of $C_2$- to $C_6$-dicarboxylic acids such as bis(2-ethylhexyl)adipate, dioctyl maleate, diisopropyl adipate, aromatic and aliphatic sulfonic acid esters such as $C_2$- to $C_{20}$-alkylsulfonic acid esters of phenol or of $C_1$- to $C_{22}$-alkanols or typical aromatic plasticisers such as polyphenyls in a wide viscosity range, including wax-like polyphenyls such as are obtainable, for example, from the Monsanto company, dibenzyltoluene, isomeric mixtures of $C_{20}$ to $C_{40}$ aromatic compounds, with preference being given to the use of mixtures of plasticisers of the ester type and aromatic type.

An example of a preferred plasticiser mixture is a mixture of acetyl tributyl citrate and dibenzyltoluene.

Likewise suitable as additives are triacyl esters of glycerol of non-animal origin. Suitable additives can comprise, for example, modified fats of vegetable origin such as hydrogenated palm oil or soybean oil or synthetic fats.

Suitable fats are described in DE 197 11 514 A1 (e.g. p. 2, line 65-p. 3, line 22; corresponding to U.S. Pat. No. 6,395, 801), to the full content of which reference is here made. Avocado oil, cottonseed oil, groundnut oil, cocoa butter, pumpkin seed oil, linseed oil, maize germ oil, olive oil, palm oil, rice oil, rapeseed oils, safflower oil, sesame oil, soybean oil, sunflower oil, grapeseed oil, wheat germ oil, Borneo tallow, fulwa butter, hemp oil, illlipé butter, lupin oils, candlenut oil, kapok oil, katiau fat, kenaf seed oil, kekuna oil, poppy seed oil, mowrah butter, okra oil, perilla oil, sal butter, shea butter and tung oil are especially suitable, provided that the fats in question have been hydrogenated before use. Suitable hydrogenated fats are considered to be those whose iodine value is less than 20 (measured in accordance with the DGF [German Society for Fat Science] standard C-V 11 Z2). Fat hydrogenation procedures are described, for example, in "Ullmanns Enzyklopädie der industriellen Chemie", 4th edition, volume 11, p. 469.

Mixtures of those naturally occurring fats, and also synthetically prepared fats such as Softisan 154 or Dynasan 118 (from Hüls) can likewise be used. The preparation of such synthetic triacyl glycerides is relatively simple for the person skilled in the art and can be carried out by starting from glycerol and the appropriate fatty acid methyl esters. Such esterification reactions are described in, inter alia, "Houben-Weyl, Methoden der Organischen Chemie", Vol. E5/Part 1, p. 659 ff.

Preferred triacyl glycerides correspond to the formula:

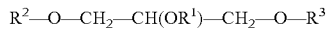

in which $R^1$, $R^2$ and $R^3$ denote, each independently of the others, $C_{11}H_{23}CO$, $C_{13}H_{27}CO$, $C_{15}H_{31}CO$ or $C_{17}H_{35}CO$. Mixtures of such triacyl glycerides also come into consideration.

Likewise suitable as additives are liquid polymeric compounds having molecular weights of more than about 2000 g/mol, for example types of compounds such as polyethers, polyesters, polyurethanes, polycarbonates or polyolefins, with hydroxyl, ether, alkyl and acyl groups being suitable as end groups.

A special compound class of liquid polymers is represented by those of the polyether type.

Polyethers which have a molecular weight the same as or similar to the polymerizable polyethers used in the dental impression material can also be used as additives. For example, dihydroxy or diacetyl polyethers comprising oxytetramethylene and oxydimethylene units in a ratio of from 4:1 to 3:1 and molecular weights in the range from about 3000 to about 8000 g/mol are suitable as additives.

Polypropylene oxide polyols and/or copolymerisation products and/or block copolymerisation products of ethylene oxide and propylene oxide having hydroxyl or acetyl end groups can also be used in admixture with the mentioned polyethers or on their own as additives.

In the case of block copolymerisation products having molecular weights greater than about 2000 g/mol, the solubility-promoting action of those surfactant-like compounds can be additionally utilised.

Furthermore, as a result of selecting and mixing the aforementioned polyether derivatives, the flow behaviour and the requisite adjustment of hydrophilicity and hydrophobicity of the mixed preparations can be decisively influenced.

The compositions according to the invention may also comprise, as additives, from about 5 to about 40% by weight or from about 10 to about 30% or from about 15 to about 25% by weight fillers having preferably reinforcing action.

For that purpose there may be used organic and inorganic solids which, in the compositions according to the invention, do not give rise to any undesirable reactions during storage and which, after mixture of separately stored components, do not adversely affect the course of setting. For example, silicic acid, zinc oxide, calcium carbonate, barium sulphate, quartz powder, heavy spar, fluorspar, calcium phosphate or kaolin are suitable for that purpose.

In that context, fillers having a $SiO_2$ content of more than about 50% by weight, for example at least about 90% by weight, such as quartz powder and fine-particle silicic acids of synthetic or natural origin, have been found to be advantageous.

For example, pyrogenic silicic acids and precipitated silicic acids, which are usually used in surface-modified form, and also diatomaceous earth from various sources are suitable.

Mixtures of processed diatomaceous earth that has a pH, in a 5% aqueous suspension, of from about 8 to about 10 and pyrogenic surface-modified silicic acid having BET surface areas of from about 100 to about 600 $m^2/g$ are especially suitable.

The preparations according to the invention may also comprise further additives such as dyes and coloured pigments, disinfectants, aromas or flavourings.

Acid capture agents, which fully neutralise acids, acid groups or acid-cleaving substances present in the starting materials, may also be used as additives. For example, amines, especially tertiary amines, are suitable for the purpose.

As additives there may also be used modifying agents as are described in DE 32 45 052 (p. 4-p. 6; corresponding to U.S. Pat. No. 4,532,268), with reference being made expressly to the modifying agents mentioned therein, which are understood as being part of the disclosure of the present text.

The above-mentioned additives are usually contained in a composition according to the invention in an amount of from 0 to about 60% by weight, for example from about 10 to about 40% by weight.

The compositions according to the invention can, in principle, be obtained in any manner known to the person skilled in the art. A preferred method for obtaining a dental impression material according to the invention is characterized in that A) a polymerizable polyether material which is selected from the group consisting of
  a) polyethers with at least one aziridino group,
  b) polyethers with at least one olefinically unsaturated group and a compound with at least one SiH group and
  c) polyethers with at least one olefinically unsaturated group and at least one SiH group and
  d) polyethers with at least one alkoxysilyl group;
  e) polyethers with at least one olefinically unsaturated group and a metal carbene and
B) about 0.01 to about 15% by weight of a random copolyether of ethyleneoxide and at least one more alkyleneoxide which is not ethylene oxide, the copolymer comprising at least about 50% of structural elements from ethylene oxide as a fluidity improver, and
  optionally one or more adjuvants selected from the group consisting of catalysts, plasticizers, fillers, softeners, dyes, pigments, solvents, disinfectants, thinners, flavorants, odorants, theological additives, emulsifiers or stabilizers are mixed.

While the constituents can generally be supplied in any number of components, it can be preferred, if the constituents are supplied as a 2-component material comprising a base paste and a catalyst paste prior to mixing. The base and catalyst paste can be mixed by any means known to the skilled person, including simple manual mixing by spatula, mixing by a manually driven dispenser or mixing by a motorized dispenser. It can be advantageous, if the constituents are mixed by a manually driven dispenser. Preferred systems are based on so-called double syringe dispenser, e.g., available from MIXPAC SYSTEMS AG Grundstrasse 12, 6343 Rotkreuz Switzerland. A typical dispensing equipment includes a 2 compartment cartridge (2:1) having an overall volume of about 50 ml, a dispensing gun and a static mixing tip. Thus, such a system allows for extruding about 50 ml of a mixed composition.

A composition according to the invention should have a consistency (according to ISO 4823:2000) of about 30 to about 40 mm, especially from about 32 to about 38 mm, materials with a consistency of about 32 to about 35 mm being classified as type 1 materials and materials with a consistency from about 35 to about 38 mm being classified as type 2 materials.

It can be preferred, if the fluidity improver is present in a composition according to the invention such that a usual manual dispenser, e.g., a dispenser as described above, can be emptied with about 40 to about 50 manual pressing cycles in less than about 60 seconds, e.g. in about 30 to 40 sec.

It has been found that mixing of the components of the invention together with the inventive fluidity improver by using a manual dispenser can also be accomplished when the polyether materials used do not have a low content of cyclic polyethers as described in US 2003/0109596.

A composition according to the invention is suitable for producing dental materials.

A catalyst component used in accordance with the invention may also comprise, in addition to one of the above-mentioned compounds or a mixture of two or more thereof, one or more additives. The additives already mentioned hereinbefore in the context of the present text are suitable as additives.

The initiator compounds of a catalyst component may be, for example, in the form of low-viscosity liquids or solids which may be difficult to incorporate uniformly in the more or less viscous masses of the base component. In order to avoid that disadvantage, the initiator compounds may be brought into a viscous form corresponding to the particular intended application area, for example by incorporating fillers of large surface area, such as colloidal silica.

Also, the use of solutions of the initiator compounds in suitable plasticisers as the catalyst component is often advantageous; by that means not only is it possible for extreme mixing ratios to be avoided but it is also possible for cross-linking agents that are solid at room temperature, e.g. acetyl tributyl citrate, to be conveniently incorporated into the catalyst component.

For example, a catalyst component that is suitable according to the invention can comprise at least one of the following classes of compounds, which bring about plasticising of the cured dental materials, namely A typical plasticisers having molecular weights of less than about 500 g/mol,
B triacyl glycerides that are solid at room temperature, having molecular weights in the range from about 500 to about 2000 g/mol, or
C polymers that are liquid at room temperature, having molecular weights of more than about 2000 g/mol, or a mixture of two or more thereof.

Initiator compounds for initiating a polymerization reaction of the polymerizable polyether compounds are generally contained in a catalyst component in an amount of from about 0.5 to about 90% by weight, for example from about 2 to about 80% by weight or from about 5 to about 50% by weight.

In order to produce the dental impression materials according to the invention, the base component and the catalyst component are mixed together in suitable quantitative ratios.

The mixing is advantageously carried out as described above.

Usually, in the case of polyether-based dental materials, the volumetric mixing ratio or the weight ratio between catalyst component and base component is adjusted to values of from about 3:1 to about 1:10, with special preference being given to adjustments of from about 1:2 to about 1:5, especially about 1:2 or about 1:5.

In the case of aziridino compounds forming the polymerizable polyether material, the molar ratio of aziridino groups to anions of the initiator compounds is, in the context of the dental materials according to the invention, from about 3:1 to about 0.9:1, for example from about 2:1 to about 1:1, especially from about 1.8:1 to about 1.2:1.

From the values mentioned it can accordingly be seen that the composition of the catalyst component and the base component can, in dependence on the desired molar ratio of the reactive aziridino groups to the anions of the initiator compound or of the mixture of two or more initiator compounds, vary within wide ranges.

The polyether-based dental impression materials according to the invention, having improved flow properties, are obtained, for example, from preparations containing, in total, about 30 to about 80% by weight, preferably about 45 to about 71% by weight, aziridino-group-carrying compounds;
about 0.1 to about 15% by weight fluidity improver,
about 8 to about 40% by weight, preferably about 10 to about 25% by weight, compounds which bring about plasticising of the cured dental materials;
about 4 to about 25% by weight, preferably about 9 to about 16% by weight, fillers;
about 4 to about 20% by weight, preferably about 4 to about 16% by weight, further active ingredients such as colorants, aromas, initiators, retarding agents, accelerators, rheological additives, consistency agents and surfactants.

The preparations according to the invention can be used in very different dental materials employed in dental medicine or dental technology. Preferred areas of use of such dental materials are single-phase and two-phase impression-taking in dental medicine and bite registration.

The invention relates also to containers and mixing devices containing materials produced from the preparations according to the invention, especially dental materials, for example cartridges, sachets, impression trays, static and dynamic mixers and mixing devices.

The invention relates also to a kit for producing dental materials, comprising at least one base component comprising a polymerizable polyether material and at least one catalyst component comprising a catalyst for the cross-linking of at least part of the polymerizable polyether material, wherein the base component or the catalyst component or both comprise about 0.1 to about 15% by weight of a random copolyether of ethyleneoxide and at least one more alkyleneoxide which is not ethylene oxide, the copolymer comprising at least about 40% of structural elements from ethylene oxide as a fluidity improver and wherein the base component and the catalyst component are present separated from one another.

Furthermore, the invention relates to the use of a composition according to the invention as basic component B for coatings, impression materials, seals or dental moulding materials.

The invention is explained in greater detail herein below by means of working examples.

Working Examples

Test Methods

Consistency

Consistency was measured according to Deutsche Industrie Norm (DIN) or European Norm (EN) Method # 4823: 2000.

Recovery from Deformation

Recovery from deformation was measured according to Deutsche Industrie Norm (DIN) or European Norm (EN) Method # 4823:2000. The specimens were left in the water bath for 3:00 minutes before conducting the measurement.

Tensile Strength (Mpa) and Elongation at Break (%)

Tensile strength and Elongation at break were measured according to Deutsche Industrie Norm (DIN) Method # 53504 (geometry S2, 200 mm/min) using Universalprüfmaschine Zwick Z020 (Zwick GmbH &Co, Ulm, Germany).

Shore A Hardness

Time dependant Shore A hardness was measured according to Deutsche Industrie Norm (DIN) Method # 53505. The curable compositions were allowed to cure for the given time at 23° C. and about 50% relative humidity before the Shore A hardness was measured.

Contact Angle

Specimens as described in Deutsche Industrie Norm (DIN) or European Norm (EN) Method # 4823:2000 used for determination of linear dimensional change were used. The curable compositions were allowed to cure for 24 hours at 23° C. and about 50% relative humidity. The cured compositions were analyzed with respect to their water contact angle using the commercially available Drop Shape Analysis System DSA 10 (Krüss GmbH-Hamburg, Germany). 25 data points per second were collected via video analysis. There was no delay from start of measurement and data collection. Data may be collected for approximately 12 seconds. Droplet size was determined on the thickness of canula: 5 µl were chosen. Contact angles were calculated using the circle fitting method. Tests were conducted in a climatized room at 23° C. Deionized water was used as the fluid. Calibration of the device was done according to manufacturer's instruction for Young-Laplace fitting prior to the measurements. Initial contact angles (contact angles obtained immediately after the water droplet has been placed) and 10-second contact angles (contact angles obtained 10 seconds after the ater droplet has been placed) were recorded.

Cyclic Extrusion Test

A 2:1 cartridge having a volume of 50 ml containing the catalyst and base paste as described below was loaded into a hand dispenser. A mixing tip was mounted. Details are given under "Mixing". The cartridge with the mounted mixing tip was placed in a holder of an Universalprüfmaschine (Fa. Zwick, type: Z 020) equipped with a 5 kN load cell. A pusher was placed in a way that it exerts a force on the driving plate of the hand dispenser in order to extrude impression material. The speed of the pusher was 100 mm/min. If a force of >2 N (software testXpet V 8.1) was recorded, the speed of the pusher was enhanced to 150 mm/min and recording of data starts. When the force was recorded to be 700 N, the pressure was reduced to 500 N by moving the pusher backwards with a speed of 300 mm/min. The measurement was finished when the driving plate/pusher has been moved forward in the cartridge by 30 mm total. Number of cycles needed as well as time was measured.

Formulations:

| Catalyst Paste: | |
|---|---|
| 19.2% | sulfonium salt tetafluoroborate (according to U.S. Pat. No. 4,167,618) |
| 40.4% | acetyl tributyl citrate (CAS-No 77-90-7, Croda Surfactants Ltd) |
| 3.5% | surfactant (copolymer EO/PO) (CAS-No 9003-11-6, C. H. Erbslöh KG) |
| 12.1% | diatomaceous earth (CAS-No 68855-54-9, Celatom MW 25, Chemag AG Frankfurt/Main) |
| 24.0% | highly dispersed silica, surface treated (CAS-No 68909-20-6, HDKH ™, Wacker) |
| 0.8% | dyes, pigments |

| Base Paste 1 | |
|---|---|
| 67.8% | difunctional aziridino polyether Mn: 6000 (from EO (ethylene oxide)/THF (tetrahydro furane) |
| 8.6% | fat (trisacylic ester of glycerine, Sasol Germany GmbH) |
| 6.9% | dibenzyl toluene (CAS-No 26898-17-9, Atofina) |
| 3.0% | N-Ethyl-ptoluenesolfonamid (CAS-No. 80-39-7, Biesterfeld) |
| 1.2% | imidazole compound (according to DE 32 45 052) |
| 12.1% | diatomaceous earth (CAS-No 68855-54-9, Celatom MW 25, Chemag AG Frankfurt/Main) |
| 0.4% | flavors, fragrances |

| Base Paste 2 | |
|---|---|
| 67.8% | difunctional aziridino polyether (polyether back bone is a copolymer EO/THF with a molecular weight of 6000) |
| 8.6% | fat (trisacylic ester of glycerine, Sasol Germany GmbH) |
| 6.9% | random copolymer EO/PO monobutylether (CAS-No 9038-95-3, Breox PAG 50 A 20, Cognis Performance Chemicals UK Ltd) |
| 3.0% | N-Ethyl-ptoluenesolfonamid (CAS-No. 80-39-7, Biesterfeld) |
| 1.2% | imidazole compound (according to DE 3245052) |
| 12.1% | diatomaceous earth (CAS-No 68855-54-9, Celatom MW 25, Chemag AG Frankfurt/Main) |
| 0.4% | flavors, fragrances |

Mixing

Base Paste 1 as well as Base Paste 2 were reacted with the Catalyst Paste in the following manner:

2 parts base paste and 1 part catalyst paste were placed in the separate chambers of a 2:1 cartridge (catridge system S-50, type CS 050-02-09, Mixpac), and sealed with stoppers (2 volume: PSA 53-02-EP, 1 volume: PSB 53-02-EP, Mixpac). The pastes were mixed using a hand dispenser (DS 53-01-00, Mixpac) and a mixing tip (MBT—7,5 12 D, Mixpac).

Measured Properties

| Base Paste used | Consistency mixed paste (DIN EN 4823:2000) [mm] | Shore A Hardness (DIN 53505) after | | | | | Tensile strength (DIN 53504) [MPa] | Elongation at Break (DIN 53504) [%] | Recovery from deformation (DIN EN 4823:2000) [%] |
|---|---|---|---|---|---|---|---|---|---|
| | | 8 min | 10 min | 15 min | 30 min | 24 hrs | | | |
| 1 | 37 | 41 | 44 | 47 | 50 | 52 | 1.97 ± 0.22 | 353 ± 54 | 98.5 |
| 2 | 37 | 41 | 44 | 47 | 50 | 52 | 1.95 ± 0.15 | 378 ± 43 | 98.5 |

-continued

| Base Paste used | Contact angle [°] | | Cyclic Extrusion | |
| --- | --- | --- | --- | --- |
| | initial | 10 sec | Time [sec] | Number of cycles |
| 1 | 84 | 60 | 29 | 7-8 |
| 2 | 76 | 53 | 23 | 4 |

The invention claimed is:

1. A kit for producing dental materials, comprising at least one base component and at least one catalyst component, the base component comprising at least one polymerizable polyether material with a linear backbone having no side chains, a plasticizer, and about 0.1 to about 15% by weight of a fluidity improver, the fluidity improver being a random copolyether of ethyleneoxide and at least one more alkyleneoxide which is not ethylene oxide, the copolymer comprising at least about 50% of structural elements from ethylene oxide, the fluidity improver having preferably a molecular weight $M_w$ in a range of about 100 to about 2000 and the at least one catalyst component comprising a catalyst for the cross-linking of at least part of the polymerizable polyether material, wherein the base component and the catalyst component are present separated from one another.

2. The kit according to claim 1, wherein the at least one polymerizable polyether material with a linear backbone having no side chains is selected from the group consisting of:
   a) polyethers with at least one aziridino group;
   b) polyethers with at least one olefinically unsaturated group and a compound with at least one SiH group;
   c) polyethers with at least one olefinically unsaturated group and at least one SiH group;
   d) polyethers with at least one alkoxysilyl group; and
   e) polyethers with at least one olefinically unsaturated group.

3. The kit according to claim 1, wherein fluidity improver is not a tenside.

4. The kit according to claim 1, wherein the fluidity improver has a molecular weight $M_w$ in a range of about 100 to about 2000.

5. The kit according to claim 1, wherein the fluidity improver is selected from the group consisting of a linear random copolymer with a molecular weight of at least 200 and at least 1 OH end group and a linear random copolymer with one or two $C_1$-$C_4$-alkyl ether endgroups or one or two $C_1$-$C_4$-alkyl ester endgroups or one $C_1$-$C_4$-alkyl ether endgroup and one $C_1$-$C_4$-alkyl ester endgroup.

6. The kit according to claim 1, wherein the fluidity improver is a liquid at 23° C. and 101.325 Pa.

7. The kit according to claim 2, wherein the at least one polymerizable polyether material with a linear backbone having no side chains comprises a polyether with two or more aziridino groups and the polyetherbackbone is a copolymer of ethyleneoxide and propyleneoxide or ethyleneoxide and butyleneoxide.

8. The kit according to claim 7, wherein the polyether with two or more aziridino groups has a molecular weight $M_w$ of more than 3000.

9. The kit according to claim 2, wherein the at least one polymerizable polyether material with a linear backbone having no side chains comprises a polyether with at least one olefinically unsaturated group and at least one compound with at least one SiH group or a polyether with at least one olefinically unsaturated group and at least one SiH group and the polyether backbone of at least one of the polyethers has a polymer backbone which is a copolymer of ethyleneoxide and propyleneoxide or ethyleneoxide and tetrahydrofurane.

10. The kit according to claim 2, wherein the at least one polymerizable polyether material with a linear backbone having no side chains comprises at least one polyether with at least one olefinically unsaturated group which is polymerizable by ROMP and the polyetherbackbone of at least one of the polyethers has a polymer back bone which is a copolymer of ethyleneoxide and propyleneoxide or ethyleneoxide and tetrahydrofurane.

11. The kit according to claim 1, wherein it contains one or more adjuvants selected from the group consisting of catalysts, plasticizers, fillers, softeners, dyes, pigments, solvents, disinfectants, thinners, flavorants, odorants, rheological additives, emulsifiers or stabilizers.

12. A method for preparing a dental impression material, said method comprising the steps of
   A) providing a polymerizable polyether material with a linear backbone having no side chains which is selected from the group consisting of
      a) polyethers with at least one aziridino group;
      b) polyethers with at least one olefinically unsaturated group and a compound with at least one SiH group
      c) polyethers with at least one olefinically unsaturated group and at least one SiH group;
      d) polyethers with at least one alkoxysilyl group; and
      e) polyethers with at least one olefinically unsaturated group and a metal carbene,
   B) mixing the polymerizable polyether material with a plasticizer and about 0.01 to about 15% by weight of a fluidity improver, the fluidity improver being a random copolyether of ethyleneoxide and at least one more alkyleneoxide which is not ethylene oxide, the copolymer comprising at least about 50% of structural elements from ethylene oxide, the fluidity improver having preferably a molecular weight $M_w$ in a range of about 100 to about 2000.

13. The method of claim 12, wherein one or more adjuvants selected from the group consisting of fillers, softeners, dyes, pigments, solvents, disinfectants, thinners, flavorants, odorants, rheological additives, emulsifiers or stabilizers are mixed with the polymerizable polyether material and/or fluidity improver.

14. The method according to claim 12, wherein the components of the dental impression materials are supplied in a base paste and a catalyst paste prior to mixing.

15. A method for obtaining a dental impression of a patient, the method comprising the steps of:
   a) providing the kit of claim 1;
   b) mixing the base component and the catalyst component of the kit of claim 1 to obtain a dental impression material;
   c) administering the dental impression material to a site in the patient's mouth;
   d) at least partially curing the material to create a dental impression; and e) retrieving the dental impression from the patient's mouth.

16. A method for preparing a plaster model of a dental situation in the mouth of a mammal or a human being, wherein a dental impression is taken according to the method of claim 15 and the dental impression is filled with plaster which is hardened and retrieved from the dental impression.

* * * * *

UNITED STATES PATENT AND TRADEMARK OFFICE
CERTIFICATE OF CORRECTION

PATENT NO. : 8,007,579 B2
APPLICATION NO. : 12/375245
DATED : August 30, 2011
INVENTOR(S) : Thomas Klettke Page 1 of 2

It is certified that error appears in the above-identified patent and that said Letters Patent is hereby corrected as shown below:

On the First Page of the Title Pages, in Column 2, under (Other Publications)
Line 18, delete "Denistry," and insert -- Dentistry, --, therefor.

Column 1
Line 45, delete "alcanyl" and insert -- alkenyl --, therefor.

Column 3
Lines 12-13, delete "polyetherbackbone" and insert -- polyether backbone --, therefor.
Lines 19-20, delete "polyetherbackbone" and insert -- polyether backbone --, therefor.
Line 28, delete "back bone" and insert -- backbone --, therefor.
Line 35, delete "theological" and insert -- rheological --, therefor.

Column 8
Line 30, delete "sulfonuim" and insert -- sulfonium --, therefor.

Column 14
Line 27, delete "theological" and insert -- rheological --, therefor.
Line 28, delete "stabilizers" and insert -- stabilizers. --, therefor.
Line 66, delete "illlipé" and insert -- illipé --, therefor.

Column 16
Line 54, delete "theological" and insert -- rheological --, therefor.

Column 19
Line 36, delete "canula:" and insert -- cannula: --, therefor.
Line 44, delete "ater" and insert -- water --, therefor.

Column 20
Line 2, delete "testXpet" and insert -- testXpert --, therefor.

Signed and Sealed this
Eighteenth Day of October, 2011

David J. Kappos
*Director of the United States Patent and Trademark Office*

CERTIFICATE OF CORRECTION (continued)
U.S. Pat. No. 8,007,579 B2

Line 14, delete "tetafluoroborate" and insert -- tetrafluoroborate --, therefor.
Line 32, delete "back bone" and insert -- backbone --, therefor.
Line 47, delete "(catridge" and insert -- (cartridge --, therefor.

Column 21
Line 55, in Claim 7, delete "polyetherbackbone" and insert -- polyether backbone --, therefor.

Column 22
Line 16, in Claim 10, delete "polyetherbackbone" and insert -- polyether backbone --, therefor.
Line 17, in Claim 10, delete "back bone" and insert -- backbone --, therefor.
Line 27, in Claim 12, delete "of" and insert -- of: --, therefor.
Line 30, in Claim 12, delete "of" and insert -- of: --, therefor.
Line 33, in Claim 12, delete "group" and insert -- group; --, therefor.